| United States Patent [19] | [11] Patent Number: 5,010,065 |
| --- | --- |
| Skuballa et al. | [45] Date of Patent: Apr. 23, 1991 |

[54] CYCLODEXTRIN CLATHRATES OF 5-CYANOPROSTACYCLIN DERIVATIVES AND THEIR USE AS PHARMACEUTICAL AGENTS

[75] Inventors: Werner Skuballa; Helmut Dahl; Helmut Vorbrueggen; Olaf Loge; Karl-Heinz Thierauch, all of Berlin, Fed. Rep. of Germany

[73] Assignee: Schering Aktiengesellschaft, Berlin and Bergkamen, Fed. Rep. of Germany

[21] Appl. No.: 276,754

[22] Filed: Nov. 28, 1988

[30] Foreign Application Priority Data

Nov. 27, 1987 [DE] Fed. Rep. of Germany ....... 3740838

[51] Int. Cl.$^5$ .................. A61K 31/335; C07D 307/93
[52] U.S. Cl. ..................................... 514/58; 536/103;
514/465; 424/493
[58] Field of Search .................. 536/103; 514/58, 465;
424/493

[56] References Cited

U.S. PATENT DOCUMENTS

| 3,816,393 | 6/1974 | Hayashi et al. | 536/103 |
| 4,219,479 | 8/1980 | Vorbrüggen et al. | 514/465 |

FOREIGN PATENT DOCUMENTS

| 64511 | 7/1975 | Australia . |
| 2840142 | 4/1979 | Fed. Rep. of Germany . |
| 2128674 | 6/1982 | Fed. Rep. of Germany . |
| 56-150039 | 4/1980 | Japan . |
| 2006193 | 5/1979 | United Kingdom . |
| 2017699 | 10/1979 | United Kingdom . |
| 2189783 | 11/1987 | United Kingdom . |

OTHER PUBLICATIONS

Chemical Abstracts, vol. 103, No. 20, 11-18-85, 1. Koji et al., "Prostaglandins and Their Cyclodextrin Complexes", 16608d, 359.
Kirk-Othmer-Concise Encyclopedia of Chemical Technology 1985, pp. 282 & 283.
Advanced Organic Chemistry Mar. 1985, pp. 79 & 80.

*Primary Examiner*—Ronald W. Griffin
*Attorney, Agent, or Firm*—Millen, White & Zelano

[57] ABSTRACT

The invention relates to cyclodextrin clathrates of 5-cyanoprostacyclin analogs.

10 Claims, No Drawings

CYCLODEXTRIN CLATHRATES OF 5-CYANOPROSTACYCLIN DERIVATIVES AND THEIR USE AS PHARMACEUTICAL AGENTS

BACKGROUND OF THE INVENTION

This invention provides cyclodextrin clathrates of 5-cyanoprostacyclins, agents containing them as well as methods of using their medicinal properties.

5-Cyanoprostacyclin analogs are pharmaceutically and medicinally valuable active ingredients, whose production and use are described, for example, in DE-OS 2753244 (U.S. Pat. No. 4,219,479). These substances have, in comparison with natural prostacyclins in a similar range of action, a substantially improved specificity and above all a substantially longer action.

The 5-cyanoprostacyclin analogs described in this prior art often are not present in crystalline form; consequently their pharmaceutical use is limited. In addition, their water solubility and rate of dissolution are limited.

SUMMARY OF THE INVENTION

It has now been found that inclusion compounds of these 5-cyanoprostacyclin analogs with cyclodextrins do not have said disadvantages or possess them to a lesser degree, i.e., their water solubility is improved, the rate of dissolution is increased, and the inclusion compounds are present in crystalline form. Moreover, their stability, for example, in regard to heat, light and oxygen is increased and their galenical preparation (e.g., production of solutions or tablets) is facilitated.

The invention thus relates to cyclodextrin clathrates of 5-cyanoprostacyclin analogs of formula I

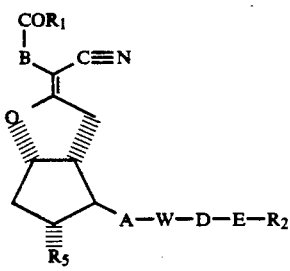

in which $R_1$ means the radical $OR_3$, and $R_3$ can mean hydrogen, alkyl, cycloalkyl, aryl or a heterocyclic radical, or the radical $NHR_4$ with $R_4$ meaning an acid radical, B means a straight-chain or branched-chain alkylene group with 2-10 C atoms, A means a —$CH_2$—$CH_2$—, cis—CH=CH—, trans-CH=CH— or —C≡C group, W means a free or functionally modified hydroxymethylene group or a free or functionally modified

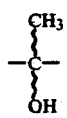

group, and the COH group can be in the alpha or beta position,

D and E together mean a direct bond or

D means a straight-chain or branched alkylene group with 1-5 C atoms,

E means an oxygen atom or a sulfur atom or a direct bond, $R_2$ means an aliphatic, cycloalkyl, or an optionally substituted aryl or heterocyclic group, $R_5$ means a free or functionally modified hydroxy group and, if $R_3$ represents hydrogen, the salts with physiologically compatible bases.

As alkyl group $R_3$ straight or branched chain alkyl groups with 1-10 C atoms are suitable, such as, for example, methyl, ethyl, propyl, butyl, isobutyl, tert-butyl, pentyl, neopentyl, heptyl, hexyl, decyl, etc. Alkyl groups $R_3$ can optionally be substituted once to several times (e.g., 1-3) by halogen atoms (e.g., F, Cl, Br, I), alkoxy groups (e.g., of 1-4 C-atoms), optionally substituted aryl groups (e.g., of 6-10 C-atoms and optionally substituted as described below), mono- or dialkylamino- (e.g., each alkyl being of 1-4 C atoms) and trialkylammonium (e.g., each alkyl group being of 1-4 C atoms). Those alkyl groups that are substituted once are preferred. Suitable substituents include, for example, fluorine, chlorine or bromine atoms, phenyl, dimethylamino, diethylamino, methoxy, ethoxy, etc. There can be mentioned as preferred alkyl groups $R_3$ those with 1-4 carbon atoms such as, e.g., methyl, ethyl, propyl, dimethylaminopropyl, isobutyl and butyl.

As aryl groups $R_3$ both substituted and unsubstituted aryl groups (e.g., of 6-10 C atoms) are suitable such as, for example, phenyl, 1-naphthyl and 2-naphthyl, which each can be substituted by 1-3 halogen atoms, a phenyl group, 1-3 alkyl groups with 1-4 carbon atoms each, a chloromethyl, fluoromethyl, trifluoromethyl, carboxyl, hydroxy or alkoxy group with 1-4 carbon atoms. Substituents in the 3 or 4 position on the phenyl ring, for example, by fluorine, chlorine, alkoxy or trifluoromethyl or the 4 position by hydroxy are preferred.

Cycloalkyl groups $R_3$ can contain 4-10, preferably 5 or 6 carbon atoms in the ring. The rings can be substituted by alkyl groups with 1-4 carbon atoms. As examples there can be mentioned cyclopentyl, cyclohexyl, methylcyclohexyl and adamantyl.

As heterocyclic groups $R_3$, 5- and 6-membered heterocycles are suitable which preferably contain at least one heteroatom (e.g., 1 or 2), preferably nitrogen, oxygen or sulfur and, e.g., are aromatic. There can be mentioned as examples 2-furyl, 2-thienyl, 2-pyridyl, 3-pyridyl and 4-pyridyl, etc.

Physiologically compatible acid radicals (acyl groups) are suitable as acid radicals $R_4$. Preferred acids are organic (e.g., hydrocarbon) carboxylic acids and sulfonic acids with 1-15 C atoms, which belong to the aliphatic, cycloaliphatic, aromatic, or aromatic-aliphatic series. Heterocyclic acids are fully equivalent for use and are fully included within the effective scope of this invention. These acids can be saturated, unsaturated and/or polybasic and/or substituted in the usual way. As examples for substituents there can be mentioned alkyl (e.g., of 1-4 C atoms), hydroxy, alkoxy (e.g., of 1-4 C atoms), oxo or amino groups and halogen atoms (F, Cl, Br, I).

For example, the following carboxylic acids can be mentioned: formic acid, acetic acid, propionic acid, butyric acid, isobutyric acid, valerianic acid, isovalerianic acid, caproic acid, heptanoic acid, caprylic acid, pelargonic acid, capric acid, undecanoic acid, lauric acid, tridecanoic acid, myristic acid, pentadecanoic acid, trimethylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and tri-chloroacetic acid, aminoacetic acid, diethylaminoacetic acid, piperidinoacetic acid, morpholinoacetic acid, lactic acid, succinic acid, adipic acid, benzoic acid; benzoic acids substituted with halogen, trifluoromethyl, hydroxy, alkoxy or carboxy groups; nicotinic acids, isonicotinic acid, furan-2-carboxylic acid, cyclopentylpropionic acid, etc. Acyl radicals with up to 10 C atoms are considered as particularly preferred, e.g., alkanoyl radicals.

Suitable as sulfonic acids are, for example, methanesulfonic acid, ethanesulfonic acid, isopropanesulfonic acid, betachloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis-(beta-chloroethyl)-aminosulfonic acid, pyrrolidino-, piperidino-, piperazino-, N-methylpiperazino- and morpholino-sulfonic acid.

Hydroxy groups $R_5$ and in W can be functionally modified, for example, by etherification or esterification, and the free or modified hydroxy groups in W can be in the alpha or beta position, and free hydroxy groups are preferred.

Radicals known to one skilled in the art are suitable as ether and acyl radicals. Easily cleavable ether radicals, such as, for example, the tetrahydropyranyl, tetrahydrofuranyl, alpha-ethoxyethyl, trimethylsilyl, dimethyl-tert-butylsilyl and tri-p-benzyl-silyl radical are preferred. As acyl radical the same ones mentioned for $R_4$ are suitable; i.e., there can be mentioned, for example, acetyl, propionyl, butyryl, benzoyl.

Straight-chain or branched-chain, saturated (e.g., alkyl) and unsaturated (e.g., alkenyl) aliphatic radicals, preferably saturated, with 1-10, especially 1-5 C atoms are suitable as aliphatic group $R_2$, which optionally can be substituted by optionally substituted aryl as defined above. As examples there can be mentioned methyl, ethyl, propyl, butyl, isobutyl, tert-butyl, pentyl, hexyl, heptyl, octyl, butenyl, isobutenyl, propenyl, pentenyl, benzyl and p-chlorobenzyl.

The cycloalkyl group $R_2$ can contain 4-10, preferably 5 and 6 carbon atoms in the ring. The rings can be substituted by alkyl groups with 1-4 carbon atoms. As examples, there can be mentioned cyclopentyl, cyclohexyl, methylcyclohexyl and adamantyl.

As substituted or unsubstituted aryl groups $R_2$ (e.g., of 6-10 C atoms) there are suitable, for example, phenyl, 1-naphthyl and 2-naphthyl, which, in each case, can be substituted by 1-3 halogen atoms, a phenyl group, 1-3 alkyl groups with 1-4 carbon atoms each, a chloromethyl, fluoromethyl, trifluoromethyl, carboxy, alkoxy or hydroxy group. Substitution in the 3 or 4 position on the phenyl ring is preferred, e.g., by fluorine, chlorine, alkoxy or trifluoromethyl or in the 4 position by hydroxy.

Suitable as heterocyclic groups $R_2$ are 5- or 6-membered heterocycles, which contain at least 1 heteroatom, preferably nitrogen, oxygen or sulfur. As examples, there can be mentioned 2-furyl, 2-thienyl, 2-pyridyl, 3-pyridyl and 4-pyridyl, i.a.

Suitable as alkylene group B are straight-chain or branched-chain, saturated and unsaturated alkylene radicals, preferably saturated with 2-10, especially 2-5 carbon atoms. As examples there can be mentioned ethylene, 1,2-propylene, ethylethylene, trimethylene, tetramethylene, pentamethylene, i.a.

Suitable as alkylene group D are straight-chain alkylene radicals with 1-5 C atoms or branched-chain saturated and unsaturated alkylene radicals with 1-5 or 2-5 C atoms. The radicals mentioned for B are suitable as examples.

For the production of the clathrates according to the invention the compounds of general formula I can be dissolved in a pharmacologically acceptable solvent, e.g., an alcohol, preferably ethanol, a ketone, e.g., acetone or an ether, e.g., diethyl ether, and mixed with aqueous solutions of alpha-, beta- or gamma-cyclodextrin, preferably beta-cyclodextrin, at 20°-80° C., or the acids of Formula I in the form of the aqueous solutions of their salts, e.g., sodium or potassium salts, can be mixed with a cyclodextrin and, after dissolution, can be mixed with the equivalent amount of an acid, e.g., hydrochloric acid or sulfuric acid.

At this point or after cooling, the corresponding clathrates crystallize out. However, it is also possible to convert oily or crystalline 5-cyanoprostacyclins of formula I, by prolonged stirring (e.g., 1 hour to 14 days) at room temperature, by treatment with an aqueous solution of cyclodextrins, into the corresponding cyclodextrin crystalline form. The clathrates can be isolated by suctioning off and drying as solid, freely flowing crystals.

By selection of suitable amounts of cyclodextrin and water, the clathrates can be obtained in stoichiometric composition having a reproducible active ingredient content. The clathrates can be used in their dry, hygroscopic form or in a hydrous, less hygroscopic form.

The starting material carbacyclins and α-, β- or γ-cyclodextrins, of course, are well known and/or readily preparable from known starting materials.

Suitable dextrins will include a wide variety of those which produce crystalline forms of carbacyclins as inclusion compounds. See, for example, J. E. F. Reynolds (ed.) Martindale, The Extra Pharmacopoeia 28th ed. The Pharmaceutical Press, London 1982,p. 333 and 389–390 and O.-A. Neumueller (ed.), Roempps Chemie-Lexikon, 8. Aufl. Franckh'sche Verlagshandlung, Stuttgart 1981, p. 763-764, 841, 1053-1054.

The new clathrates of 5-cyanoprostacyclins according to formula I are in stoichiometric ratio of carbacyclin: cyclodextrin or have a higher cyclodextrin portion. The preferred stoichiometric ratio of carbacyclin: cyclodextrin (beta, preferably) is 1:2 or 1:3. For example, 5-cyano-16-methylprostacyclin with beta-cyclodextrin forms a complex of the composition 1:2.5 (12.12% of the prostacyclin) or any lower values.

In a preferred class of compounds of this invention, $AWDER_2$ is:

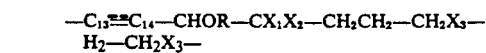

wherein

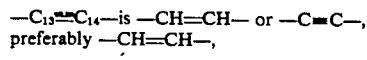

preferably —CH=CH—,

R is H or a protective group as described above, preferably H, $X_1$ and $X_2$ independently are H, $CH_3$ or $C_2H_5$, and at least one of $X_1$ and $X_2$ is other than H, preferably one is H and the other $CH_3$, $X_3$ is H, $CH_3$ or $C_2H_5$, preferably H.

The clathrates produced according to this invention are valuable pharmaceutical agents.

The clathrates of this invention cause lowering of blood pressure and bronchodilation. Further they are suitable for inhibition of thrombocyte aggregation. They act cytoprotectively on the stomach, intestines, heart, liver, kidneys and pancreas. Consequently, the new cyclodextrinclathrates of formula I represent valuable pharmaceutical agents. Moreover, with a similar range of action, they exhibit a higher specificity and above all a substantially longer action, in comparison with corresponding prostaglandins.

In comparison with $PGI_2$, they are marked by a greater stability. The high tissue specificity of the new prostaglandins is shown in the examination of smooth-muscle organs, such as, for example, on the guinea pig ileum or on the isolated rabbit trachea, where a substantially lesser stimulation is to be observed than in the application of natural prostaglandins of the E, A or F type.

The new 5-cyanoprostacyclin clathrates have the properties typical for prostacyclins, such as, for example, reduction of the peripheral arterial and coronary vascular resistance, inhibition of thrombocyte aggregation and dissolution of platelet thrombi, myocardial cytoprotection and thus reduction of the systemic blood pressure without reducing at the same time cardiac output and coronary blood flow; treatment of stroke, prophylaxis and therapy of coronary diseases, coronary thrombosis, myocardial infarct, peripheral arterial diseases, arteriosclerosis and thrombosis, prophylaxis and therapy of ischaemic attacks of the CNS system, shock therapy, inhibition of bronchoconstriction, inhibition of gastric acid secretion, cytoprotection of the stomach and intestinal mucosa, cytoprotection in the liver, kidneys, heart and pancreas, also in organ transplantations, antiallergic properties, reduction of pulmonary vascular resistance and of pulmonary blood pressure, promotion of kidney blood flow, use instead of heparin or as adjuvant in dialysis or hemofiltration, preservation of banked blood plasma, especially banked blood platelets, inhibition of labor pains, treatment of gestational toxicosis, increasing cerebral blood flow, etc. Moreover, the new carbacyclin clathrates have antiproliferative and antidiarrheagenic properties. The carbacyclins of this invention can also be used, for example, in combination with beta blockers or diuretics.

The 5-cyanoprostacyclin clathrates of this invention can also be used in combination, e.g., with beta blockers, diuretics, phosphodiesterase inhibitors, calcium antagonists, nonsteroidal inflammation inhibitors, leucotriene synthetase inhibitors, leucotriene antagonists, thromboxane synthetase inhibitors or thromboxane antagonists.

The clathrates according to the invention can be used in liquid or solid galenical formulations, and formulations can be administered enterally, parenterally, vaginally or rectally or they can also be incorporated in surgical suture material and in synthetic resins.

For production of tablets, the prostaglandin cyclodextrin clathrate can be mixed with vehicles and auxiliary agents such as lactose, corn starch, polyvinylpyrrolidone and magnesium stearate.

For production of solutions for enteral and parenteral application, the aqueous cyclodextrin clathrate solutions are freeze-dried together with lactose. Then the freeze-dried products can be brought to the desired concentration with physiological saline solution.

Therefore, the invention involves pharmaceutical preparations and formulations, which contain a cyclodextrin clathrate of a carbacyclin analog as active ingredient.

Their use is entirely analogous to the known carbacyclins per se, e.g., nileprost. Thus, they can be administered in typical dosages of 1-1500 $\mu g/kg/day$ (using unit dosages, e.g., of 0.01-100 mg) to treat the foregoing conditions.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application P. 37 40 838.0, filed Nov. 27, 1987, are hereby incorporated by reference.

EXAMPLES

Example 1

490 mg of 5-cyano-16-methylprostacyclin (Nileprost) is stirred with 14.16 g of beta-cyclodextrin in 100 ml of water for 5 days at 24° C. The solid is suctioned off and dried for 8 hours at 0.1 torr and 24° C. 10.7 g of freely flowing crystals of beta-cyclodextrin clathrate of 5-cyano-16-methyl-prostacyclin is obtained. The content of prostacyclin analog in the clathrate was determined by high-pressure liquid chromatography and was 4%.

Example 2

1.038 g of 5-cyano-16-methylprostacyclin is dissolved in 34.5 ml of 0.1N sodium hydroxide solution and diluted with 319 ml of water. Then 12.49 g of beta-cyclodextrin is added and heated to 35° C. to dissolution. It is cooled to 30° C. and in doing so is slowly mixed with 34.5 ml of 0.1N hydrochloric acid. It is stirred for 18 hours at 22° C. and 7 hours with ice cooling, is suctioned off and the solid is washed with water chloride free. It is dried in a vacuum until the crystallizate at ambient temperature and atmospheric humidity again takes up water and leaves the weight constant.

8.5 g of the beta-cyclodextrin complex of 5-cyano-16-methyl prostacyclin is obtained with stoichiometric composition 1:2.5 as hydrate in the form of a freely flowing powder, the active ingredient content in the complex, after titration, is 12.2% (calculated on anhydrous substance), the water content 7.1%.

Example 3

943 mg of beta-cyclodextrin is dissolved at 22° C. in 65 ml of water and a solution of 76.3 mg of 5-cyano-16-methyl-prostacyclin in 0.4 ml of ethanol is slowly instilled into it. It is stirred for 18 hours at 22° C. and for 5 hours in an ice bath. The crystallate is suctioned off and washed with ice cold water, acetone and again with water. It is dried in a vacuum on phosphorus pentoxide and 535 ml of a freely flowing, hygroscopic crystallate is obtained, which exhibits an active ingredient content of 12.2% determined by titration.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A cyclodextrin clathrate of a 5-cyanoprostacyclin of the formula I

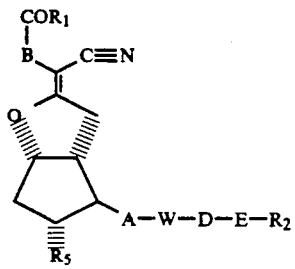

wherein $R_1$ is $OR_3$ or $NHR_4$;

$R_3$ is hydrogen; $C_{1-10}$-alkyl; $C_{1-10}$-alkyl substituted by halo, $C_{1-4}$-alkoxy, $C_{6-10}$-aryl, $C_{6-10}$ aryl substituted as defined below for $R_2$, mono- or di-($C_{1-4}$-alkyl)-amino, or tri ($C_{1-4}$-alkyl)ammonium; $C_{4-10}$cycloalkyl; $C_{4-10}$-cycloalkyl substituted by $C_{1-4}$-alkyl; $C_{6-10}$-aryl; $C_{6-10}$-aryl substituted as defined for $R_2$ below; or an aromatic heterocycle of 5- or 6-members containing 1 or 2, O, S or N hetero atoms;

$R_4$ is an acyl group of a $C_{1-15}$-hydrocarbon carboxylic or sulfonic acid;

B is alkylene of 2-10 C atoms,

A is —$CH_2$—$CH_2$—, cis—CH=CH—, trans—CH=CH— or —C≡C—;

W is RO-methylene or

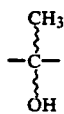

the OR group being in the alpha or beta position;

R is H or $C_{1-15}$-acyl derived from a hydrocarbon carboxylic acid, or is tetrahydropyranyl, alpha-ethoxyethyl, tetrahydrofuranyl, trimethylsilyl, tribenzylsilyl, or dimethyl-tert-butylsilyl;

D and E together mean a direct bond; or

D is alkylene of 1-5 C atoms;

E is oxygen, sulfur or a direct bond;

$R_2$ is alkyl of 1-10 carbon atoms; alkenyl of 2-10 C-atoms; $C_{1-10}$-alkyl or $C_{2-10}$-alkenyl substituted by $C_{6-10}$-aryl or $C_{6-10}$-aryl substituted as defined for substituted $C_{6-10}$-aryl below; cycloalkyl of 4-10 carbon atoms; $C_{4-10}$-cycloalkyl substituted by $C_{1-4}$-alkyl; aryl of 6-10 carbon atoms; $C_{6-10}$-aryl substituted by 1-3 halogen atoms, a phenyl group, 1-3 alkyl groups each of 1-4 carbon atoms, or a chloromethyl, fluoromethyl, trifluoromethyl, carboxy, $C_1$-$C_4$-alkoxy or hydroxy group; or an aromatic heterocycle of 5- or 6-members containing 1 or 2 O, S, or N hetero atoms; and $R_5$ is OR;

or when $R_3$ is hydrogen, a physiologically acceptable salt thereof with a base.

2. 5-cyano-16-methyl-prostacyclin-beta cyclodextrin clathrate.

3. A pharmaceutical composition comprising a compound of claim 1 and a pharmaceutically acceptable carrier.

4. A pharmaceutical composition of claim 3, wherein the compound is 5-cyano-16-methyl-prostacyclinbeta cyclodextrin clathrate.

5. A compound of claim 1, wherein said cyclodextrin is α-, β- or γ-cyclodextrin.

6. A compound of claim 5, wherein said cyclodextrin is β-cyclodextrin.

7. A method of treating an indication treatable by administering to a patient an effective amount of a 5-cyanoprostacyclin comprising administering thereto the 5-cyanoprostacyclin in the form of a cyclodextrin clathrate of claim 1.

8. A compound of claim 1, wherein $AWDER_2$ is:

wherein

—$C_{13}$=$C_{14}$—is —CH=CH— or —C≡C—;

R is H or a protective group as described above;

$X_1$ and $X_2$ independently are H, $CH_3$ or $C_2H_5$, and at least one of $X_1$ and $X_2$ is other than H;

$X_3$ is H, $CH_3$ or $C_2H_5$.

9. A method of claim 7, wherein said clathrate is 5-cyano-16-methyl-prostacyclin-beta cyclodextrin clathrate.

10. A compound of claim 8, wherein

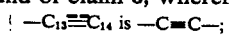

R is H;

one of $X_1$ and $X_2$ is H and the other is $CH_3$, and $X_3$ is H.

* * * * *